US008696643B2

(12) United States Patent
Knightingale et al.

(10) Patent No.: US 8,696,643 B2
(45) Date of Patent: Apr. 15, 2014

(54) SANITARY GARMENT AND METHOD FOR MAKING SAME

(76) Inventors: Cher Anne Caylin Knightingale, Toronto (CA); Ellis Charles Hanna Knightingale, Toronto (CA)

( * ) Notice: Subject to any disclaimer, the term of this patent is extended or adjusted under 35 U.S.C. 154(b) by 556 days.

(21) Appl. No.: 12/131,607

(22) Filed: Jun. 2, 2008

(65) Prior Publication Data

US 2009/0299313 A1 Dec. 3, 2009

(51) Int. Cl.
*A61F 13/15* (2006.01)

(52) U.S. Cl.
USPC .............. 604/399; 604/385.14; 604/385.15; 604/395; 604/398; 604/402

(58) Field of Classification Search
USPC .................. 604/393–402, 385.14–385.14
See application file for complete search history.

(56) References Cited

U.S. PATENT DOCUMENTS

| 5,395,355 | A  | * | 3/1995  | Wadman        | 604/370    |
| 5,814,037 | A  | * | 9/1998  | Coates        | 604/393    |
| 6,605,071 | B1 | * | 8/2003  | Gray et al.   | 604/385.28 |
| 6,764,477 | B1 | * | 7/2004  | Chen et al.   | 604/385.14 |
| 7,166,095 | B1 | * | 1/2007  | Coates        | 604/385.19 |
| 7,629,501 | B2 | * | 12/2009 | Labit et al.  | 604/372    |
| 2002/0010452 | A1 | * | 1/2002 | Dupuy       | 604/385.14 |
| 2003/0181885 | A1 | * | 9/2003 | Harkness    | 604/391    |
| 2005/0159722 | A1 | * | 7/2005 | Cheng       | 604/367    |
| 2005/0202741 | A1 | * | 9/2005 | Onodera et al. | 442/189 |

FOREIGN PATENT DOCUMENTS

| CN | 101724932 A | 6/2010 |
| CN | 101920030 A | 12/2010 |

OTHER PUBLICATIONS

Allproducts.com, Acelon Chemicals & Fiber Corporation, Bamboo Charcoal Yarn, 2013.*
Ochaco TM, Characteristics of White Bamboo Charcoal, 2010.*
Qing Shan Li et al., Preparation and Characterization of White Bamboo Charcoal PET Fiber, Chinese Chemical Letters 21,Nov. 27, 2009, pp. 1-4.
MT MERU PTE Ltd, Taketaro, Natural Living Natural Life, Mysterious Power, Interesting Facts, 2007, 6 pgs, http://www.mtmeru.com/bamboo-charcoal/bamboo-charcoal-interesting-facts.html.
Stafford Textiles Limited, Letter to Whom It May Concern dated Oct. 23, 2012, 1 pg.
E-mail exchange with inventors and Staftex, dated May 2013, 5 pgs.
E-mail exchange with inventors and Paiho, dated May 2013, 8 pgs.
E-mail exchange with inventors and Liahren, dated May 2013, 3 pgs.

* cited by examiner

*Primary Examiner* — Lynne Anderson

(57) ABSTRACT

A reusable sanitary garment is provided, having a three-part construction, incorporating an outer garment portion, a sling portion, and at least one pad, supported within the sling, which, in turn, is affixed to, and supported within, the outer garment. Both the outer garment portion and the sling portion are preferably fabricated, in an ecologically sustainable manner, from recycled plastics materials. The at least one pad may be fabricated as a reusable, washable article, or may be fabricated as a disposable article, preferably from recycled, and easily recyclable or biodegradable materials. The outer garment portion, the sling portion and/or the reusable pad may be fabricated to incorporate bamboo charcoal material, having enhanced antibacterial, deodorant, wicking and absorptive qualities.

20 Claims, 8 Drawing Sheets

SANITARY GARMENT AND METHOD FOR MAKING SAME

BACKGROUND OF THE INVENTION

1. Field of the Invention

The present invention relates to personal sanitary products and methods for fabricating same.

2. The Prior Art

In a time of raised ecological awareness, consumers are turning away from products that had been introduced in disposable formats, and are returning to renewable or reusable forms of these same products.

This principle holds true for personal sanitary products, such as are used for babies and adults with continence issues. Before the advent of disposable sanitary products, simple cloth diapers were commonly used. These, of course, became soggy or soiled quickly and required constant monitoring and changing, and subsequent laundering. The addition of rubberized or otherwise water-resistant or waterproofed outer garments alleviated some of the need for constant changing, but only partly.

The introduction of disposable sanitary garments of various configurations eliminated the need for laundering, and, depending upon the complexity of the construction of the particular sanitary garment product, some of the need for constant monitoring or changing. Some sanitary garment products even contained externally visible (upon wetting) indicia to provide evidence of the need for changing of the sanitary garment.

However, such disposable sanitary products, which are sold and used in prodigious quantities by the consuming public, use up vast quantities of "virgin" resources, including non-renewable petroleum-based resources. These disposable sanitary products, in turn, upon their use, must be disposed of, typically using up ever more limited landfill space.

As the consuming public becomes more ecologically aware, however, it seeks to turn away from disposable products, and instead turns toward products produced from renewable or at least more sustainable resources.

It would be desirable, therefore, to provide a personal sanitary product which is capable of being fabricated using renewable or sustainable resources which nonetheless is convenient to use, and performs well.

SUMMARY OF THE INVENTION

The present invention comprises, in part, a sanitary garment, having an outer garment portion, operably configured to be positioned on a wearer's body, and releasably affixed thereto. A sling portion is operably configured to be removably retained within the outer garment portion. At least one absorbent pad is removably disposed within the sling portion.

The outer garment portion and the sling portion are configured to be reusable, and fabricated from washable materials.

At least one of the outer garment portion and the sling portion is fabricated from materials, one constituent of which comprises white bamboo charcoal material, for enhanced resistance to bacteria, odor, and with enhanced absorptive performance.

DETAILED DESCRIPTION OF THE INVENTION

Figure 1:
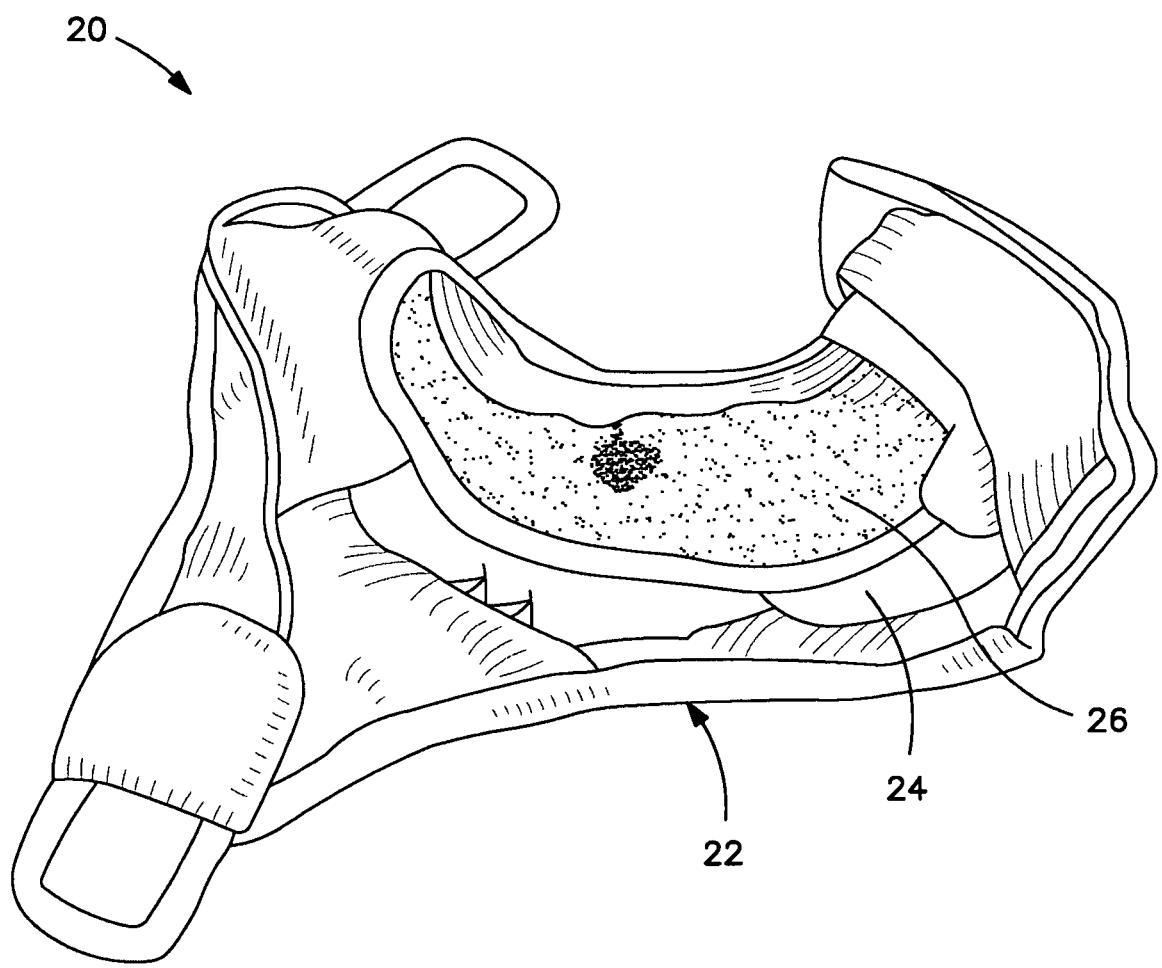
FIG. 1 is a perspective view of a sanitary garment, according to an embodiment of the invention.

While this invention is susceptible of embodiment in many different forms, there is shown in the drawings, and described in detail herein, one embodiment, with the understanding that the present disclosure is to be considered an exemplification of the principles of the invention and is not intended to limit the invention to the embodiment illustrated.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are, references to the same embodiment; and, such references mean at least one of the embodiments.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the disclosure or of any exemplified term. Likewise, the disclosure is not limited to various embodiments given in this specification.

Unless otherwise defined, all technical and scientific terms used herein have the same meaning as commonly understood by one of ordinary skill in the art to which this disclosure pertains. In the case of conflict, the present document, including definitions will control.

FIGS. 1-11 illustrates sanitary garment constructions, in accordance with the principles of the present invention. Sanitary garment 20 includes, in embodiments of the invention, outer garment portion 22, sling portion 24 and pad 26. In embodiments of the invention, all three components are releasably separable from one another, and in embodiments of the invention, at least the outer garment portion 22 and sling portion 24 are washable and reusable. In other embodiments of the invention, all three components are washable and reusable.

Outer garment portion 22, in turn, includes an outer shell 28, which, in embodiments of the invention, is fabricated from plastic fabric, e.g., polyester microfiber fabric. Such material can be obtained in an ecologically sensitive ("green") manner, from, e.g., recycled plastic beverage bottles. Such recycled plastic material may be, e.g., a recycled polyester Jersey material, sold as Staftex-ER-75D, manufactured and sold by Stafford Textiles Limited of Toronto, Ontario, Canada.

In embodiments of the invention, outer shell 28 may be a two-ply laminate of the aforementioned material, further having a breathable film lamination on the outer surface thereof, e.g., ether TPU (thermoplastic polyurethane), which itself preferably will be fabricated from recycled polyester plastic material. This outer film will also provide a stain release finish to the outer shell. Preferably, outer shell 28 will be provided with a smooth, "hard" surface finish, to provide a smooth comfortable feel to the skin, similar to other undergarment constructions. Other suitable, preferably sustainable materials may be employed, so long as they provide suitable performance, including liquid water resistance, air and moisture vapor breathability and stain resistance characteristics. Outer shell 28 may be fabricated of material that is waterproof and not merely water resistant, and yet breathable.

Lining 30 is preferably likewise fabricated from recycled, "green" materials, e.g., but is provided in a different configuration, being a polyester tricot material (e.g., Staftex-T3044, made and sold by Stafford Textiles Limited, mentioned hereinabove or material offered under the trademark ECOWIX by Mabu Naturals International, Inc., of Toronto, Ontario, Canada), having a softer, fleece-like consistency. Recycled polyester bottle material may be used. Lining 30 further includes an additional constituent, a material known as "bamboo charcoal", which is added to provide enhanced moisture absorption, breathability, odor and germ (antibacterial) resistance. Bamboo charcoal is believed, because of its microporous construction, to facilitate in wicking moisture from the wearer's skin, and to potentially facilitate the breakdown of odor-causing substances, and further to resist the buildup of static electricity. The white bamboo charcoal is implemented in the form of a yarn which is incorporated into the polyester tricot material.

Embodiments of the present invention employ microfiber fabric material in which a significant constituent is "tax" or "white" bamboo charcoal-impregnated polyester yarn, in one embodiment comprising 72% recycled polyester and 28% bamboo charcoal. While bamboo charcoal material is known, this material in the prior art has been black and dark colours, and has been used, for example, as components in ink, and was not generally suitable for use as a structural constituent in a main body portion of a sanitary garment, inasmuch as dark colors are often associated in the mind of a consumer with dirt, soil and generally unsanitary conditions.

Figure 2:
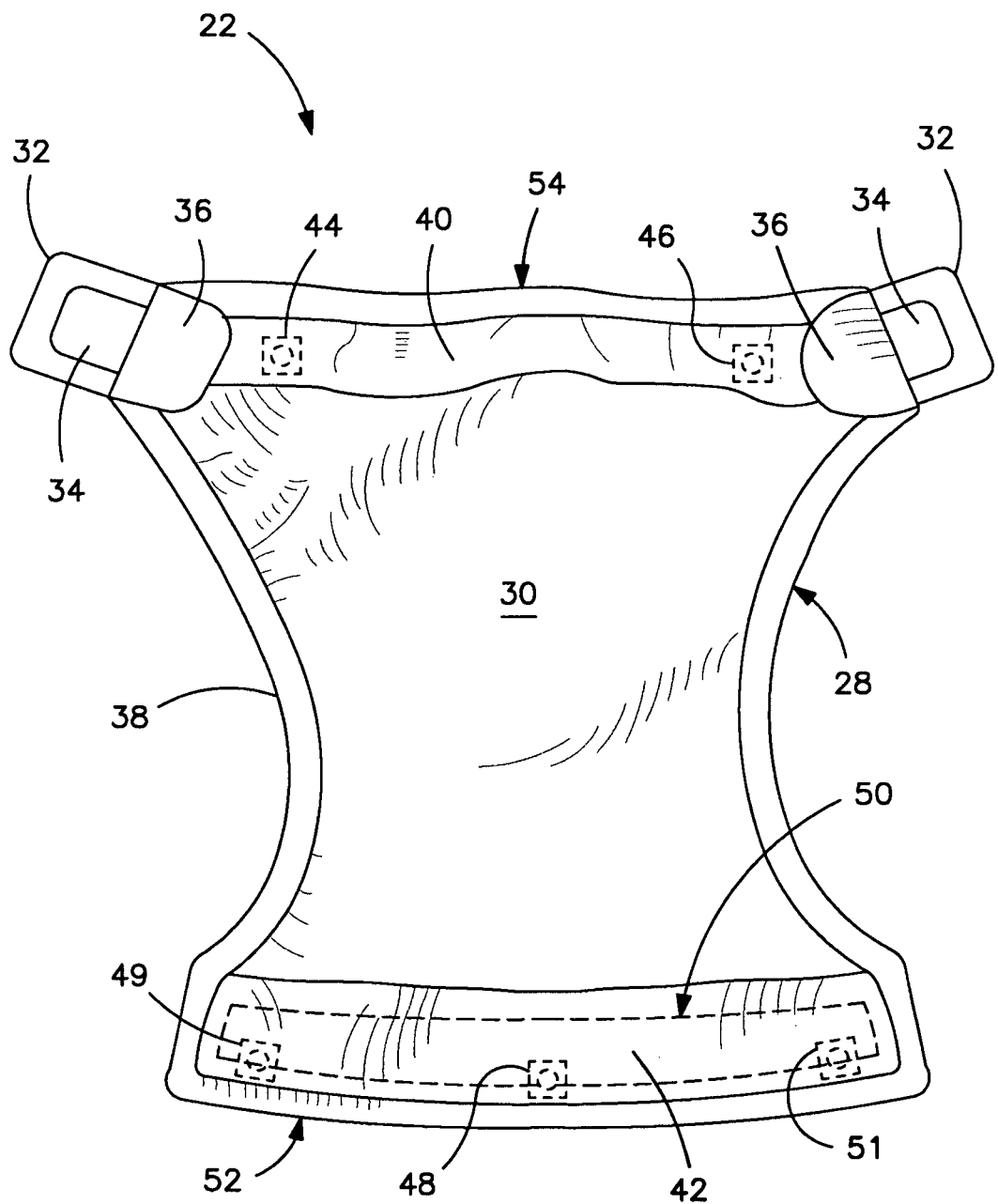
FIG. 2 is a top plan view of the outer garment portion of a sanitary garment, according to an embodiment of the invention.
Figure 3:
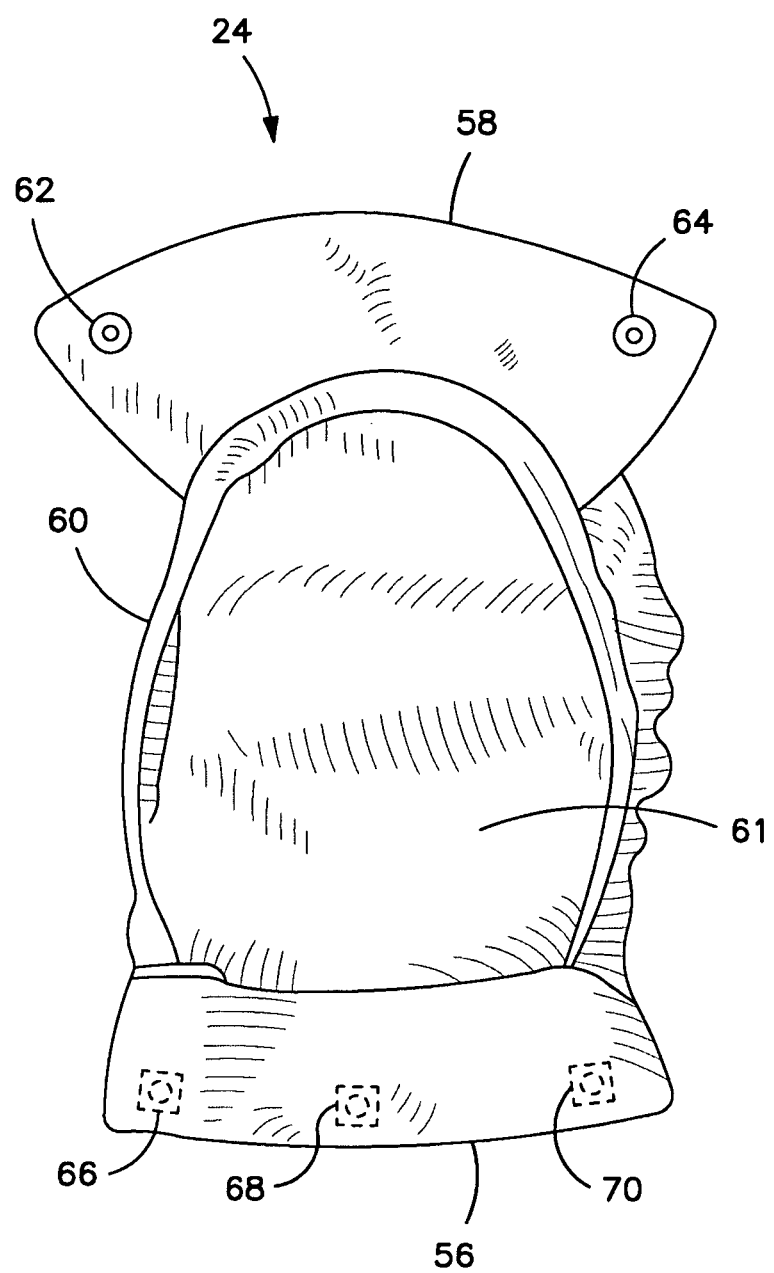
FIG. 3 is a top plan view of the sling portion of a sanitary garment, according to an embodiment of the invention.

Referring to FIG. 2, outer garment portion 22 may be provided with a general "sanitary garment-shaped" outline. Fastening tabs 32 are provided, which may be covered with cooperative fastener material 34, such as the "hook" part of "hook and loop" fastener material. Laundry pads 36 are provided adjacent fastening tabs 32, to enable fastening tabs 32 to be folded back down to adhere to the reinforced inner lining while sanitary garment 20 is "open", to enable sanitary garment 20 to be laundered, without danger of fastening tabs 32 snagging on other articles of clothing or other fabric items. Lining 30 may be attached to outer shell 28 by any suitable method, such as by rolling over the edge of outer shell 28, and stitching the two layers together to form a seam, e.g., at 38. Seam 38 may be elasticized to provide for a contoured fit, using known sanitary garment/sanitary garment construction techniques.

Material panels 40, 42 (made from the same material as sling 24) provide enclosure and cover for the ends of sling portion 24. Fasteners, e.g., "male" snap fastener parts 44, 46, 48, 49, and 51 are provided (e.g., snap fasteners manufactured and marketed by Prym of Great Britain), being positioned under fold-overs 40, 42, for securement of sling portion 24. In particular, fastener parts 44 and 46 are located on the underside of panel 40, while fastener parts 48, 49 and 50 are located on the upper (viewer-facing, as FIG. 2 is seen) surface of lining 30, beneath panel 42. Cooperative fastener strip 50 is disposed on the outer surface of outer shell 28, for engagement by fastener tabs 32, when sanitary garment 20 is in actual use. The front end of outer shell 28 is indicated at 52, and the rear end of outer shell 28 is indicated at 54.

Sling portion 24 is preferably fabricated from 100% polyester with a clear polyurethane coating. Embodiments of the invention may incorporate sling portions 24 fabricated from a material known as Staftex-GTN-N303, also marketed by Stafford Textiles Limited, which is polyester material. As with the outer shell, a polyurethane coating may be applied to the polyester layer(s) of sling portion 24. Preferably, sling portion 24 has a cradle- or canoe-shaped configuration, with folded-over front end 56, and folded-over rear end 58 being provided to receive and retain the ends of pad 26. Sling portion 24 may be fabricated of material that is waterproof and not merely water resistant, and yet breathable. Sling portion 24 further incorporates seam 60, which may be elasticized in any suitable manner, as well as pocket 61, for receipt of pad 26. Fasteners 62, 64 (which may be "female" snap fastener components), may be positioned on the outer, viewer-facing surface of fold-over 58, while fasteners 66, 68, 70 (which may likewise be "female" snap fastener components) are positioned on an upwardly facing surface of sling portion 24, under fold-over 60.

Figure 4:
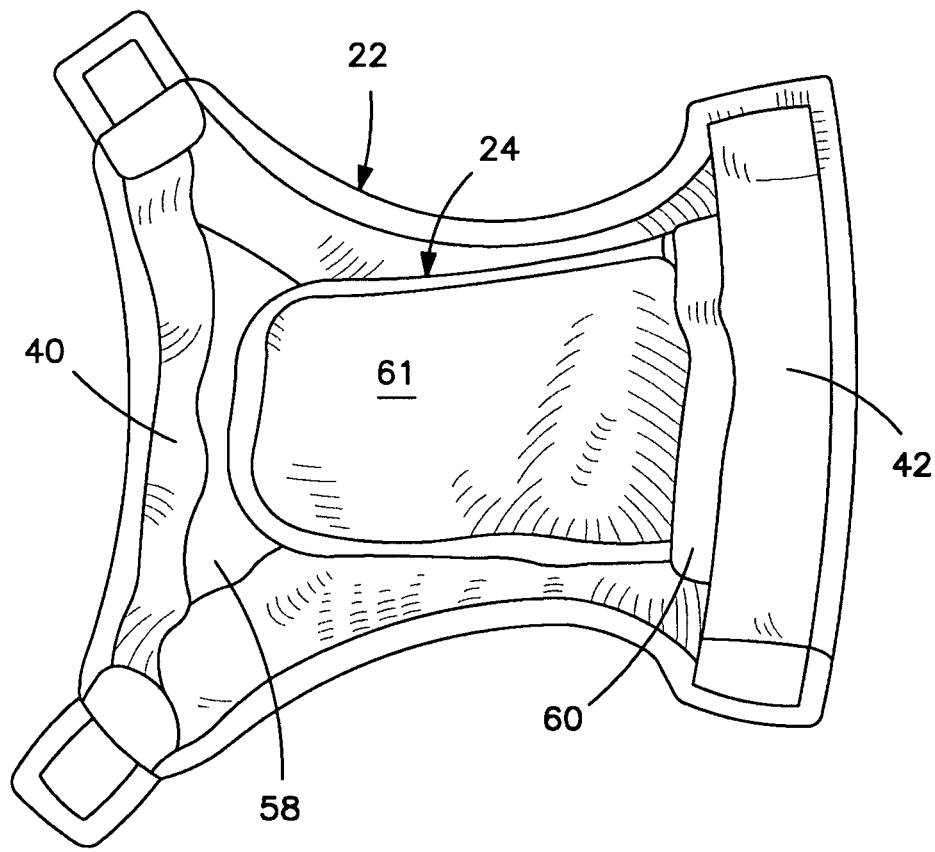
FIG. 4 is a top plan view of the outer garment of FIG. 2, with the sling portion of FIG. 3 installed, according to an embodiment of the invention.
Figure 5:
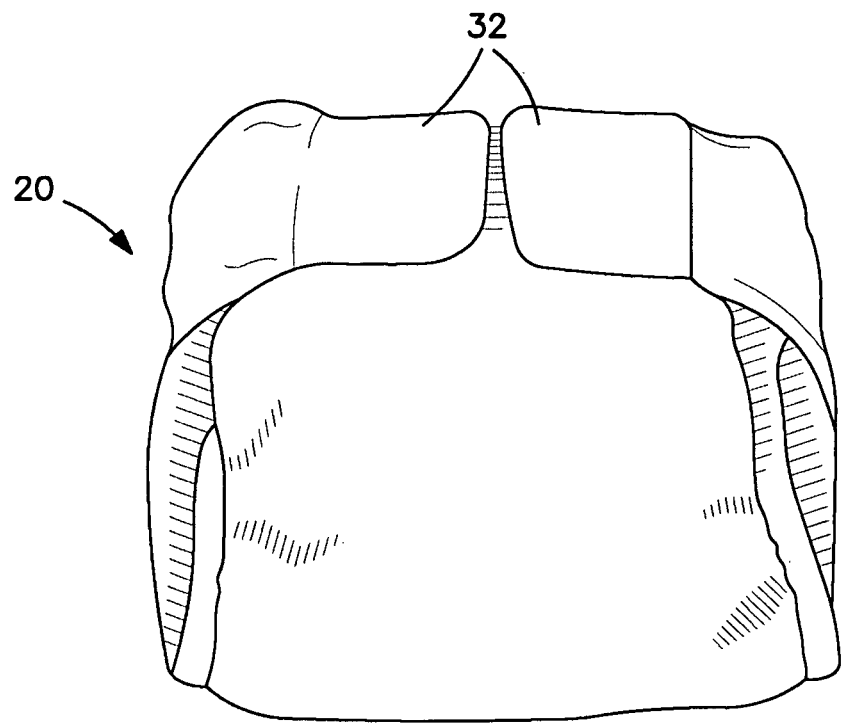
FIG. 5 is a front elevation of a sanitary garment, according to an embodiment of the invention, shown in a configuration as it would be placed on a wearer.
Figure 6:
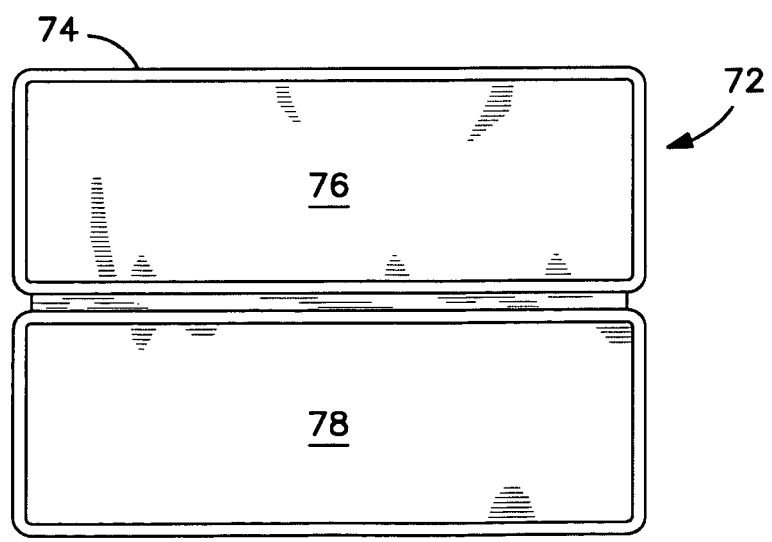
FIG. 6 is a top plan view of a washable pad for the sanitary garment, according to an embodiment of the invention.
Figure 7:
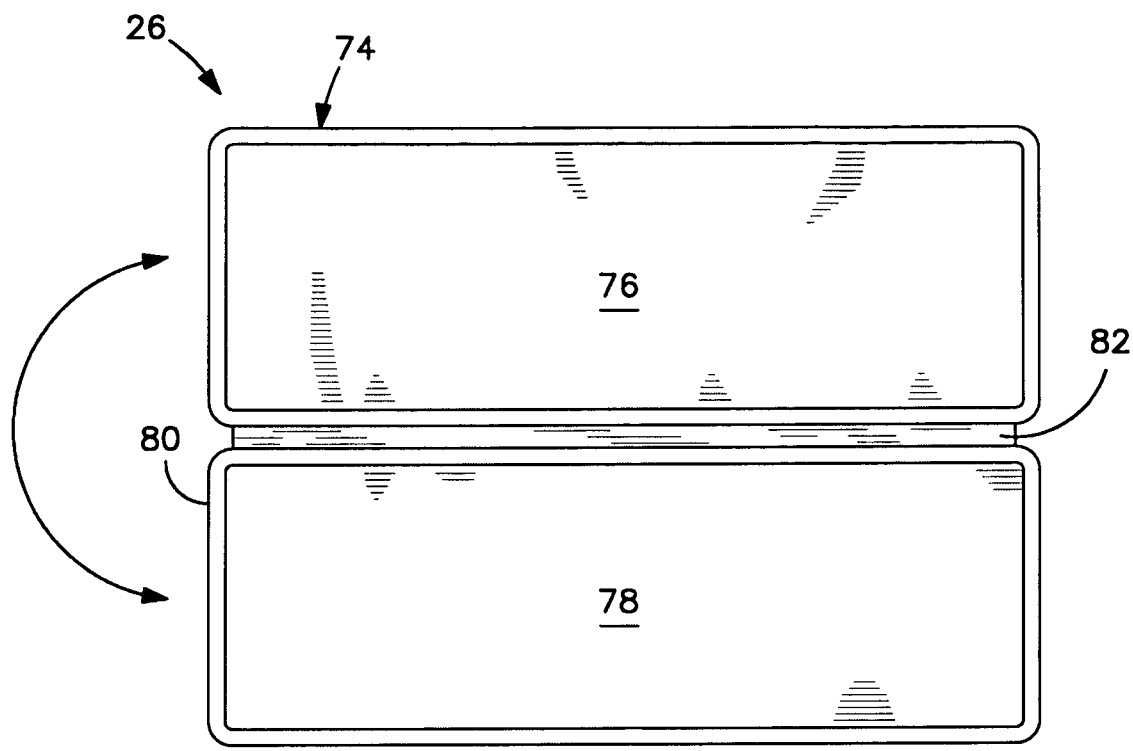
FIG. 7 is a top plan view of a pad for the sanitary garment, according to an embodiment of the invention, shown in an open configuration, exposing inner surfaces thereof.
Figure 8:
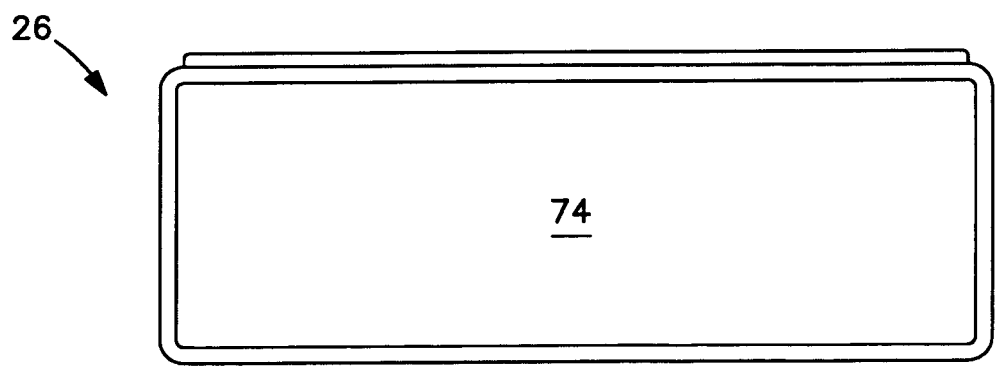
FIG. 8 is a top plan view of the pad of FIG. 7, shown in a closed configuration, exposing an outer surface thereof.

Sling portion 24 is shown installed in outer garment portion 22, in FIG. 4. Ends 58, 60 of sling portion 24 are shown tucked underneath fold-overs 40, 42 of outer garment portion 22, with fasteners 44, 46, 52, 48, 51 being mated with and joined to fasteners 62, 64, 66, 68, 70, respectively. Sanitary garment 22 is shown in FIG. 5, in the configuration it would acquire upon placement on a wearer.

Pads 26 (FIGS. 1, 7-11) and washable pads 72 (FIGS. 6, 10-11) are provided for absorption and direct contact with the wearer's body. Pads 26, which may also be used as a booster, may be fabricated from disposable (preferably readily biodegradable and otherwise ecologically sustainable) materials, such as a pad construction that comprises up to 80% biodegradable material.

Figure 9:
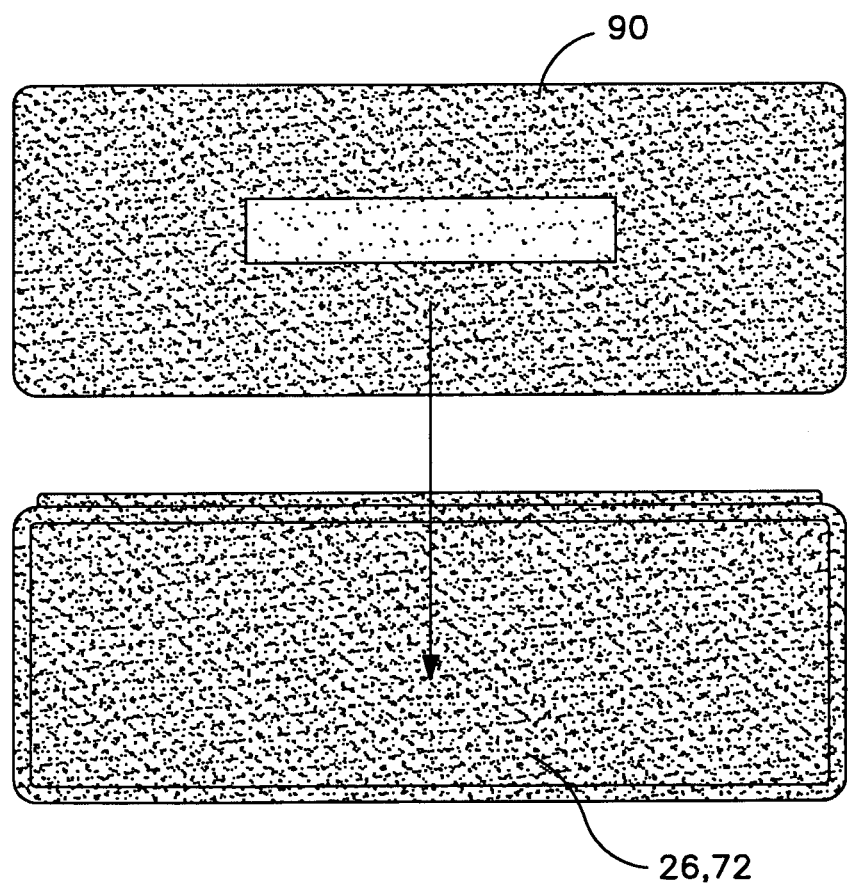
FIG. 9 is a plan view of a liner for use with a pad, according to an embodiment of the invention, shown alone and in combination with a pad.

Alternatively, pads 26 may be fabricated from washable, reusable materials. For example, pads 26 may incorporate an outer lining portion 74, fabricated from recycled polyester fabric, such as that described above, impregnated with bamboo charcoal material, for the same reasons and to obtain the same performance, as discussed hereinabove with respect to lining 30. To outer lining portion 74 are attached two spaced apart terrycloth panels 76, 78 (e.g., 80% polyester, 20% polyamide microfiber terrycloth material for enhanced absorbent characteristics, e.g. Staftex-ZF-330T, sold by Staftex Textiles), surrounded by seam 80, and separated by gap 82. In alternative embodiments of the invention, other reusable, washable materials, may be employed if desired. In use, pad 72 is preferably folded with terrycloth panels 76, 78 "facing" inwardly, to act as a reservoir for liquid wicked away from the wearer's skin by outer lining portion 74. Pads 26 may further include an inner core fabricated from Rayon viscose, cotton or bamboo charcoal to increate the rewet absorptive qualities. FIG. 9 illustrates that a further disposable fabric in either hydrophilic polypropylene or flushable rayon viscose liner may be used to surround pads 26, 72, prior to placement within sling portion 24, for facilitating removal of solid waste materials, and, when used in combination with reusable pads, subsequent washing of the pad.

Figure 10:
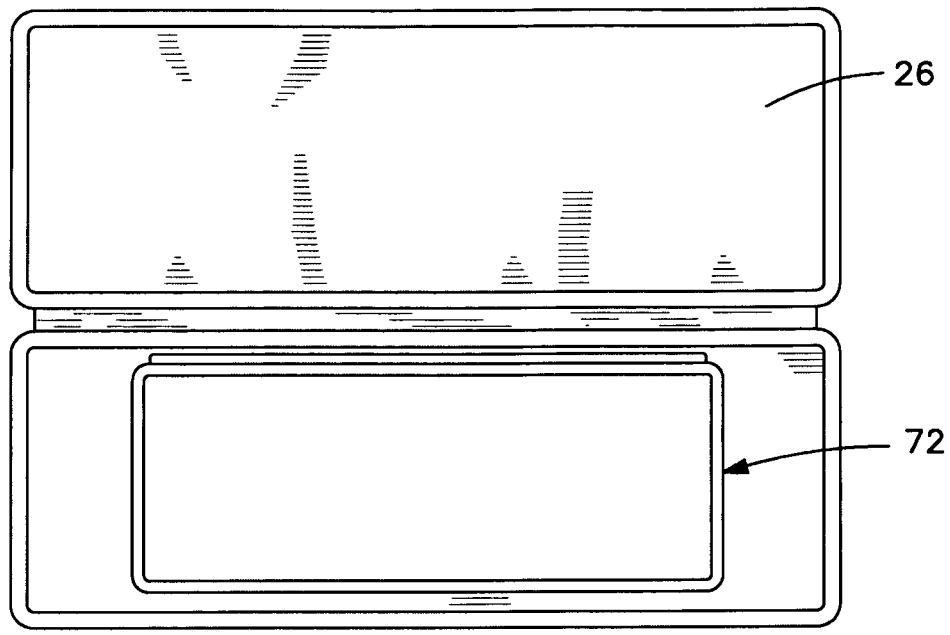
FIG. 10 is a plan view of a smaller pad (used as a booster) in combination with a full size pad, in an arrangement suitable for female children.
Figure 11:
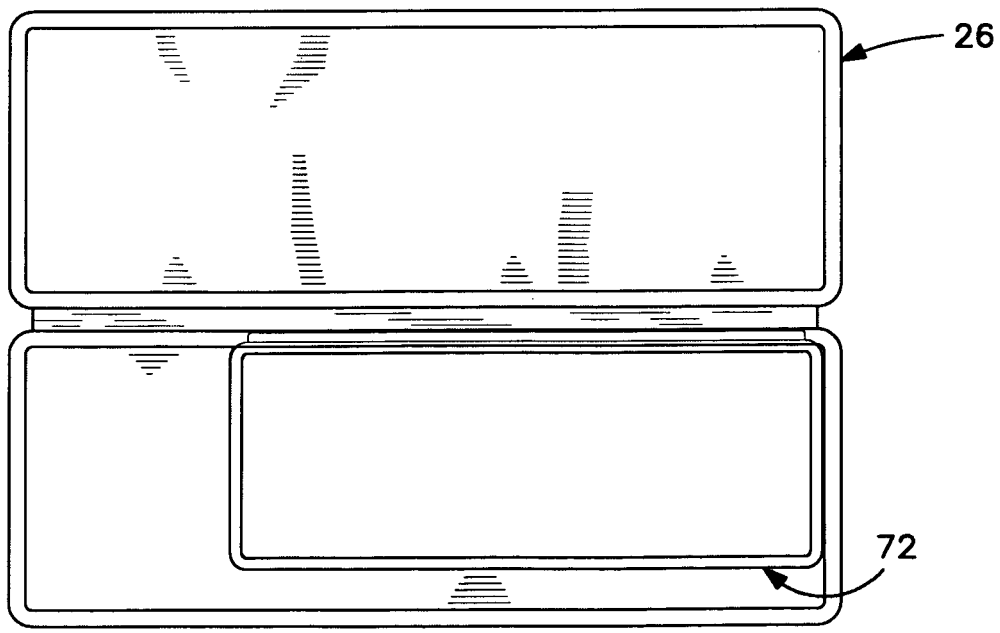
FIG. 11 is a plan view of a smaller pad (used as a booster) in combination with a full size pad, in an arrangement suitable for male children.

Booster pads 72 are essentially smaller versions of pads 26, and likewise incorporate outer lining portions 74, and absorbent panels 76, 78. The use of booster pads 72 is shown in FIGS. 10, 11, with respect to providing additional, strategically placed absorbent material, for the smallest infants. When used in association with boys, booster pads 72 will be positioned toward the front of pad 26 (FIG. 11); whereas when used in association with girls, booster pads 72 will be positioned more centrally with respect to pad 26 (FIG. 10).

In alternative embodiments of the invention, outer shell 28, sling portion 24 and/or outer lining 74 may be fabricated from alternative materials, other than recycled plastics materials, having similar water-resistance and breathability, such as the treated PTFE material sold under the trademark GORE-TEX® W. L. Gore & Associates.

The foregoing description and drawings merely explain and illustrate the invention, and the invention is not limited thereto, except as those skilled in the art who have the present disclosure before them will be able to make modifications and variations therein without departing from the scope of the invention.

What is claimed is:

1. A sanitary garment, comprising:
    an outer garment portion, operably configured to be positioned on a wearer's body, and releasably affixed thereto;
    a sling portion, operably configured to be removably retained within the outer garment portion; and
    at least one absorbent pad, removably disposed within the sling portion, wherein the sling portion comprises a pocket for receiving said absorbent pad, a front end, and a rear end; wherein said rear is provided with rear snaps on an upwardly facing surface for attachment to said outer portion, and said front end comprises a folded-over portion and is provided with front snaps for attachment to said outer portion, said front snaps being provided on an upwardly facing portion that are covered by the folded-over portion;
    at least the outer garment portion and the sling portion, being configured to be reusable, and fabricated from washable materials,
    at least one of the outer garment portion and the sling portion being fabricated from materials, one constituent of which comprises white bamboo charcoal material.

2. The sanitary garment according to claim 1, wherein the outer garment portion comprises:
    an outer shell; and
    a softer, fleece-like lining.

3. The sanitary garment according to claim 2, wherein the outer shell comprises:
    at least one layer of polyester material; and
    a thermoplastic polyurethane film layer.

4. The sanitary garment according to claim 3, wherein the at least one layer of polyester material is fabricated from recycled materials.

5. The sanitary garment according to claim 2, wherein the lining is fabricated, at least in part, from a polyester tricot material fabricated at least in part from recycled polyester material.

6. The sanitary garment according to claim 5, wherein the polyester tricot material incorporates white bamboo charcoal polyester yarn.

7. The sanitary garment according to claim 2, wherein the outer shell is fabricated of breathable waterproof material.

8. The sanitary garment according to claim 1, wherein the sling is fabricated at least in part from recycled polyester material.

9. The sanitary garment according to claim 8, wherein the sling further includes a polyurethane coating.

10. The sanitary garment according to claim 1, wherein the at least one pad is fabricated as a reusable article and fabricated from washable materials.

11. The sanitary garment according to claim 1, wherein the at least one absorbent pad comprises:
    an outer liner fabricated, at least in part, from a smooth polyester fabric layer; and
    at least one textured cloth panel affixed to the outer liner.

12. The sanitary garment according to claim 11, wherein the smooth polyester fabric layer includes, as a constituent, white bamboo charcoal polyester yarn.

13. The sanitary garment of claim 11, wherein the at least one textured cloth panel comprises a terrycloth panel.

14. The sanitary garment of claim 13, wherein the terrycloth is fabricated from at least one of: recycled polyester, polyamide.

15. The sanitary garment according to claim 1, wherein the at least one absorbent pad is fabricated from materials which are at least one of: disposable, at least partially recycled, biodegradable.

16. The sanitary garment according to claim 1, wherein the outer garment portion further comprises;
    a front end section,
    a rear end section, and
    cooperative fastening elements disposed at the front and end sections.

17. The sanitary garment according to claim 16, wherein the cooperative fastening elements comprise:

fastener tabs emanating from side edge regions of the rear end section of the outer garment portion, having pads having hook elements disposed thereon, a band of cooperative loop material disposed on an outwardly-facing surface of the front end section of the outer garment portion, whereupon positioning of the sanitary garment on a wearer's body, the fastener tabs are wrapped around the wearer's body to be brought into contact and co-adhered to the band of cooperative loop material, for maintaining the sanitary garment on the wearer's body.

18. The sanitary garment according to claim 17, further comprising:

laundry tab sections, disposed adjacent the fastener tabs, in the rear end section of the outer garment section, and having cooperative loop material disposed thereon, to enable the fastener tabs to be folded onto the laundry tab sections, to enable the outer garment section to be laundered, while precluding undesired and inadvertent snagging of the fastening tabs on other articles being laundered.

19. The sanitary garment according to claim 1, wherein the white bamboo charcoal material comprises approximately 72% recycled polyester material and approximately 28% bamboo charcoal material.

20. The sanitary garment according to claim 6, wherein the white bamboo charcoal polyester yarn comprises approximately 72% recycled polyester material and approximately 28% bamboo charcoal material.

* * * * *